(12) United States Patent
Gray et al.

(10) Patent No.: US 9,204,797 B2
(45) Date of Patent: *Dec. 8, 2015

(54) GAIT-BASED BIOMETRIC SYSTEM FOR DETECTING PATHOMECHANICAL ABNORMALITIES RELATING TO DISEASE PATHOLOGY

(71) Applicants: Todd D. Gray, Ottawa (CA); Vladimir Polotski, Ottawa (CA); Barry Smale, Ottawa (CA)

(72) Inventors: Todd D. Gray, Ottawa (CA); Vladimir Polotski, Ottawa (CA); Barry Smale, Ottawa (CA)

(73) Assignee: AUTONOMOUS ID CANADA INC., Ottawa, Ontario (CA)

( * ) Notice: Subject to any disclaimer, the term of this patent is extended or adjusted under 35 U.S.C. 154(b) by 208 days.

This patent is subject to a terminal disclaimer.

(21) Appl. No.: 13/939,923

(22) Filed: Jul. 11, 2013

(65) Prior Publication Data
US 2014/0159911 A1    Jun. 12, 2014

Related U.S. Application Data

(63) Continuation-in-part of application No. 13/581,633, filed on Dec. 6, 2012.

(51) Int. Cl.
*G05B 19/00*    (2006.01)
*G08C 19/16*    (2006.01)
(Continued)

(52) U.S. Cl.
CPC .............. *A61B 5/0024* (2013.01); *A43B 3/00* (2013.01); *A61B 5/1038* (2013.01); *A61B 5/6807* (2013.01); *A61B 2562/046* (2013.01)

(58) Field of Classification Search
CPC .... A61B 5/1038; A61B 5/1114; A61B 5/112; A61B 5/6807; A61B 5/726; A61B 5/1036; A61B 5/0002; G07C 9/00158; G06K 9/00348; G05B 1/00; A43B 3/0005
USPC .............. 340/5.52, 870.01, 658, 944, 870.26; 382/116, 115; 702/70, 66, 150; 324/73.12, 76.13

See application file for complete search history.

(56) References Cited

U.S. PATENT DOCUMENTS

| | | | |
|---|---|---|---|
| 4,812,976 A | 3/1989 | Lundy | |
| 6,360,597 B1 * | 3/2002 | Hubbard, Jr. | ................... 73/172 |

(Continued)

FOREIGN PATENT DOCUMENTS

| | | |
|---|---|---|
| WO | 2004021883 A1 | 3/2004 |
| WO | 2004092915 A2 | 10/2004 |
| WO | 2010096907 A1 | 9/2010 |

OTHER PUBLICATIONS

Yamakawa; "Biometric Personal Identification Based on Gait Pattern Using Both Feet Pressure Change", Automation Congress, 2008, Sep. 2008.*

(Continued)

*Primary Examiner* — Mirza Alam
(74) *Attorney, Agent, or Firm* — Brion Raffoul

(57) ABSTRACT

Systems and methods for diagnosing a user's condition based on his gait. A sensor module with multiple sensors is placed inside a user's shoe and biometric data is gathered from the sensors when the user takes a step or walks. The data is used to generate loops as the various sets of data is plotted against each other. The loops obtained from the data are then compared against stored loops previously obtained. Based on the results of the comparison, the user's condition is diagnosed using predetermined indicators of specific health issues. Using the biometric data, it can be determined whether the user has a specific condition, whether a specific condition is worsening, or whether a specific condition is improving.

15 Claims, 7 Drawing Sheets

(51) Int. Cl.
 A61B 5/00 (2006.01)
 G01D 7/00 (2006.01)
 A43B 3/00 (2006.01)
 A61B 5/103 (2006.01)

(56) References Cited

U.S. PATENT DOCUMENTS

| 2002/0107649 A1* | 8/2002 | Takiguchi et al. ............... 702/75 |
| 2005/0288609 A1 | 12/2005 | Warner et al. |
| 2006/0080551 A1* | 4/2006 | Mantyjarvi et al. .......... 713/186 |
| 2008/0287832 A1 | 11/2008 | Collins et al. |
| 2009/0058855 A1* | 3/2009 | Mishra et al. ................. 345/427 |
| 2010/0324455 A1* | 12/2010 | Rangel et al. ................. 600/592 |
| 2011/0282828 A1* | 11/2011 | Precup et al. .................. 706/54 |

OTHER PUBLICATIONS

Kong, Kyoungchul et al., "A Gait Monitoring System Based on Air Pressure Sensors Embedded in a Shoe", IEEE/ASME Transactions on Mechatronics, vol. 14, No. 3, Jun. 2009.

Yamakawa, Takeshi et al., "Biometric Personal Identification Based on Gait Pattern Using Both Feet Pressure Change", Automation Congress, 2008. WAC 2008. World, pp. 1-6, Sep. 28, 2008-Oct. 2, 2008.

Huang, Bufu et al., "Gait Modeling for Human Identification", 2007 IEEE International Conference on Robotics and Automation, Roma, Italy, Apr. 10-14, 2007.

Chedevergne, Fany et al., "Development of a Mechatronical Device to Measure Plantar Pressure for Medical Prevention of Gait Issues", Proceedings of the 2006 IEEE International Conference on Mechatronics and Automation, Jun. 25-28, 2006, Luoyang, China.

Boulgouris et al, "Biometrics: Theory, Methods, and Applications", Wiley-IEEE, Nov. 2009, Chapter 18.

Morris, Stacy et al., "Shoe-Integrated Sensor System for Wireless Gait Analysis and Real-Time Feedback", Proceedings of the Second Joint EMBS/BMES Conference, Houston, TX, Oct. 23-26, 2002.

Gafurov, Davrondzhon et al., "Biometric Gait Authentication Using Accelerometer Sensor", Journal of Computers, vol. 1, No. 7, Oct./Nov. 2006.

International Searching Authority, International Search Report for PCT/CA2010/001002.

International Searching Authority, Written Opinion of the International Searching Authority for PCT/CA2010/001002.

International Searching Authority, International Preliminary Report on Patentability for PCT/CA2010/001002.

* cited by examiner

GAIT-BASED BIOMETRIC SYSTEM FOR DETECTING PATHOMECHANICAL ABNORMALITIES RELATING TO DISEASE PATHOLOGY

TECHNICAL FIELD

The present invention relates to a gait based biometric system used for the detection of the progression or regression of known pathological conditions associated to disease states and prescribed pharmacological and therapeutic treatments. More specifically, the present invention relates to a diagnostic system based on biometric loop signature formation with data comparison being performed in conjunction with an insole insert in a shoe.

BACKGROUND OF THE INVENTION

The increase in activity in the mobile healthcare and user discrete diagnostic fields have highlighted some shortcomings of current diagnostic systems and as well as of generally prescribed pharmacological and therapeutic treatments after diagnosis.

Diagnostic systems generally come in a number of categories. X-ray and MRI systems use large magnetic and nuclear isotope imaging platforms which, when used, diagnoses the user's condition using imaging techniques common to those systems and devices. Less cumbersome and intrusive diagnostic devices and methods include thermometers and other biosensing devices which measure temperature, weight, pulse rate, as well as a plethora of other biological and physiological indicators. These indicators are used when searching for signs of health, fitness level, and disease. The ancient medicinal art of reflexology has historical efforts focused on disease pathology and the feet. Adverse reactions to prescribed pharmacological and therapeutic treatments of disease are known to adversely affect a person's balance and, as a consequence, that person's gait as well.

The above noted diagnostic systems have their drawbacks. Specifically, X-ray and MRI systems are extremely large and use controlled substances such as nuclear medical isotopes. Similarly, thermometers and other biosensing devices are area specific, limited in scope and use, and require more active participation and knowledge from the user. These and other current systems have been seen as either too invasive or too cumbersome for some people to use.

There is therefore a need for a diagnostic system that is neither invasive nor linear in scope and use. As well, such a diagnostic system is preferably wearable and mobile in nature and not be vulnerable to power failures within a select timeframe. It is also preferred that the diagnostic system have the facility to measure and assess the user's unique biometric loop signature data at any time interval for instantaneous comparison against a stored loop signature.

SUMMARY OF INVENTION

The present invention provides systems and methods for diagnosing a user's condition based on his gait. A sensor module with multiple sensors is placed inside a user's shoe and biometric data is gathered from the sensors when the user takes a step or walks. The data is used to generate loops as the various sets of data is plotted against each other. The loops obtained from the data are then compared against stored loops previously obtained. Based on the results of the comparison, the user's condition is diagnosed using predetermined indicators of specific health issues. Using the biometric data, it can be determined whether the user has a specific condition, whether a specific condition is worsening, or whether a specific condition is improving.

In one embodiment, the user's biometric data is, preferably, previously extracted from his gait. The previously gathered data, and the plotted loops derived therefrom, can be used as a baseline for the user. Subsequent biometric data sets gathered from the user can then be compared against the baseline. Depending on the comparison results, a progression or regression of a user's condition can be determined. Data gathered from the general population can be used to establish any correlation between a person's changing gait as he or she progresses or regresses in a specific health condition. The treatment effects of prescribed pharmacological and/or therapeutic remedies can also be determined using the biometric data from the user as the user progresses in his or her treatment. Periodic gathering of the user's biometric data can be used to track and monitor the effects of the treatment on the user's gait to establish any causal link between the treatment regime and the user's gait. Such links and the specific effects of the treatment regime can then be used to further heighten the effectiveness of shoe based biometric data gathering devices as diagnostic tools.

In a first aspect, the present invention provides a method for determining changes in a user's medical condition using a foot-based gait device, said device having a plurality of sensors for gathering gait-based data, the method comprising:
a) selecting two of said plurality of sensors;
b) gathering data from each sensor selected in step a);
c) correlating data gathered from said two sensors such that data points gathered at similar instances are matched with one another to result in data pairs;
d) determining at least one characteristic loop from said data pairs, each characteristic loop being a loop formed when said data point pairs are plotted;
e) retrieving signature characteristic data, said signature characteristic data being derived from data resulting from biometric data previously gathered from said user;
f) determining a signature characteristic loop from said signature characteristic data;
g) comparing characteristics of said at least one characteristic loop determined in step d) with characteristics of said signature characteristic loop determined in step f);
h) in the event a comparison of said characteristics compared in step g) produces results not within predetermined limits, determining that a change has occurred in said user's medical condition;
i) in the event a comparison of said characteristics compared in step g) produces results within predetermined limits, determining that a change has not occurred in said user's medical condition.

In a second aspect, the present invention provides a system for diagnosing a change in a user's condition, the system comprising:
   a sensor module comprising at least one sensor for gathering gait-based biometric data from said user
   a data storage module for storing data relating to a signature loop, said signature loop being a loop resulting from a plot of data pairs derived from data gathered from said sensor module when said user uses said system
   a data processing module for receiving data from said sensor module, said data processing module being for determining characteristic loops from said data received from said sensor module and for comparing characteristics of said characteristic loops with characteristics of said signature loop wherein a change in said user's medical condition is indicated when said characteristics of said characteristic loops are not within predetermined limits of said characteristics of said signature loops.

In a third aspect, the present invention provides for use of an insole for use with a user's shoe to determine if a change has occurred in a user's medical condition, said insole comprising a plurality of sensors for measuring and detecting force applied by said user on different parts of said insole.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
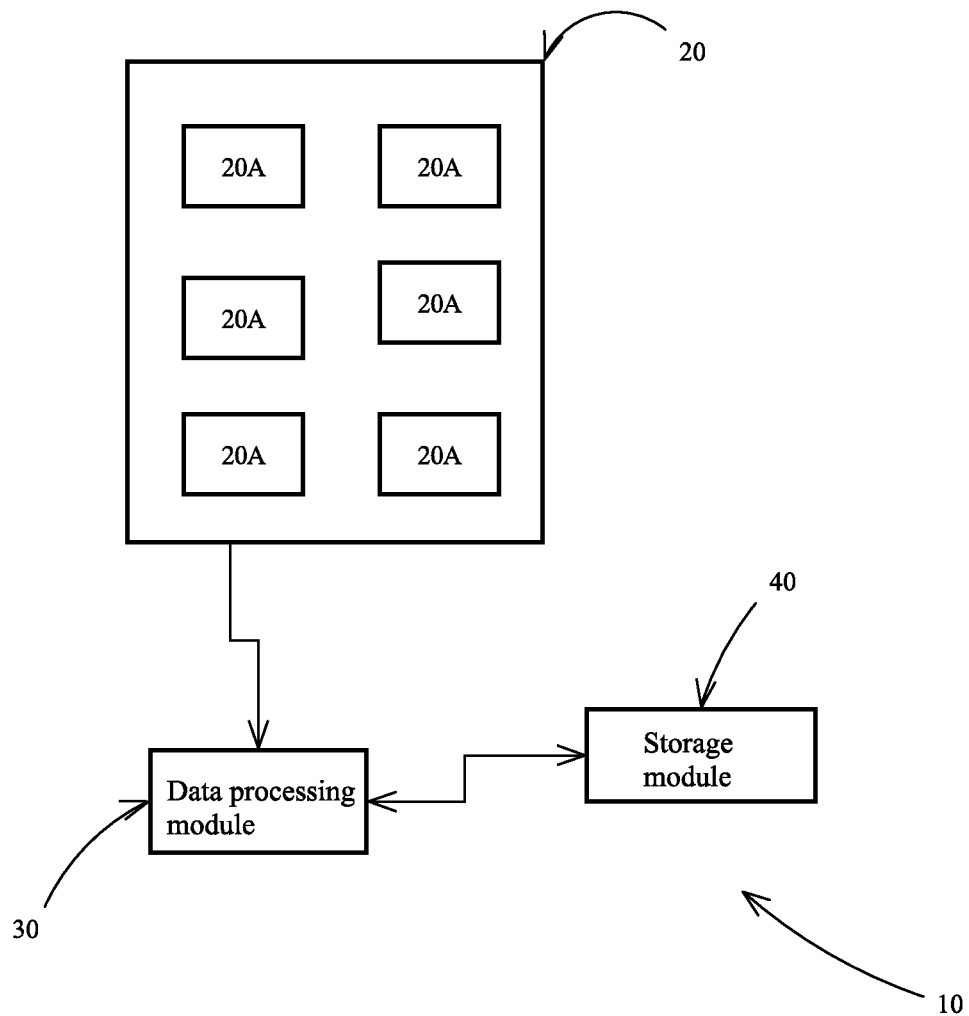
FIG. 1 is a block diagram of the system according to one aspect of the invention.

Referring to FIG. 1, a block diagram of one embodiment of the present invention is illustrated. As can be seen, the system 10 includes a sensor module 20 coupled to a data processing module 30 and which may receive data from a storage module 40. In broad terms, the sensor module 20, having multiple sensors 20A, generates biometric data from the sensors (biometric data based on the user's gait) which is then sent to the data processing module 30. The data processing module 30 then processes the biometric data and retrieves signature data from the storage module 40. The signature data comprises data that was previously gathered from the user who is currently being diagnosed. The data processing module then compares the signature data with the biometric data gathered from the multiple sensors. If there are differences between the newly gathered data and the previously gathered data, the data processing module then determines if the differences are in line with known patterns which would indicate progression or regression of a known user health condition or which would indicate a new health condition.

Optionally, the system may include a communications module 50 that is coupled to the data processing module 30. The communications module 50 may send and/or receive communications regarding the comparison between the signature data and the data gathered from the sensors. The communications module 50 may send the data gathered to the data processing module 30 such that the data processing is performed remote from the user and/or the sensor module 20.

It should be noted that the sensor module 20 has multiple sensors which gather data regarding a person's gait. In one embodiment, the sensor module is an insole positioned inside the user's shoe, with the insole having multiple discrete force sensors that detect the amount of force or pressure exerted on a section or region of the insole. With multiple regions on the insole and at least one sensor positioned on each region, a user's gait can be profiled as being the amount of pressure that that user exerts on each region over time as the user takes a step. A variant of this sensor module would have at least one strain gauge positioned such that the pressure exerted on each of the multiple regions of the foot are detected by the gauge with each region corresponding to a section of the strain gauge. With such an arrangement, each section of the strain gauge thus acts as a different discrete sensor.

It should be noted that, in one embodiment, two insoles are used per user. This way, gait data may be gathered for each user foot. Data gathered from the user's left foot may be processed differently from data gathered from the user's right foot. Alternatively, another embodiment only uses a single insole such that only one set of data is gathered per user. While the description below relates to a single insole, for a two insole embodiment, both insoles would be similar to one another and would, preferably, each conform to the description and principles outlined below.

Figure 2A:
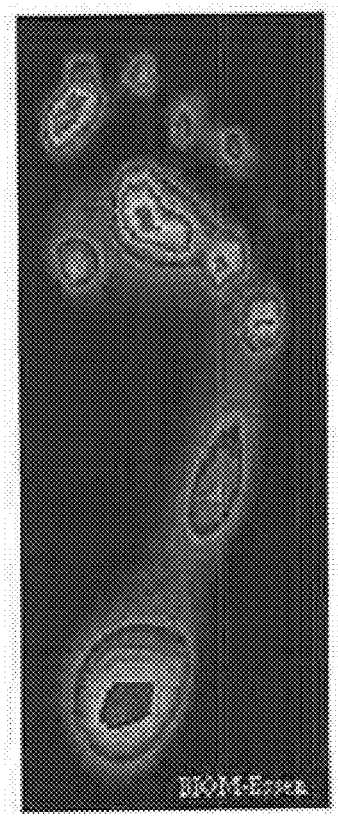
FIG. 2A is an image illustrating the different forces applied by a human foot as it takes a step.
Figure 2B:
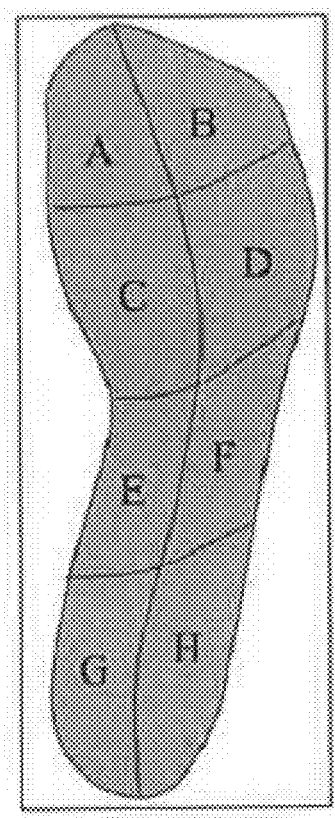
FIG. 2B is a diagram illustrating different zones on an insole according to one embodiment of another aspect of the invention.

Referring to FIGS. 2A and 2B, a schematic illustration of a number of discrete pressure zones on an insole is illustrated. FIG. 2A shows an imprint of a human foot and the unique pressure points for a specific person. FIG. 2B illustrates the location of 8 specific pressure zones or areas on one embodiment of a pressure sensing insole. Each zone in FIG. 2B has a pressure sensing pad or sensor assigned to it such that the pressure exerted on each zone can be measured. A variant of this sensor module would have, instead of discrete sensor pads at each zone, a single strain gauge positioned as described above.

In the above embodiment, each sensor in the sensor module produces a signal linearly proportional to the force being applied to the sensor. Preferably, each sensor or zone would have a data channel dedicated to its readings for transmitting those readings to the data processing module. Alternatively, in one implementation, the readings can be time division multiplexed on to a single data line from the sensor module to the data processing module. In this implementation, the data is passed through a single A/D converter to produce multiplexed channels, one for each sensor. Of course, while there are eight zones in FIG. 2B, other variants may have more or less than eight zones.

Regarding the data stream produced when the user is walking, in one embodiment, each sensor produces several hundred samples equating to approximately ten steps taken by the user. This data stream is then saved and examined by the data processing module and the actual step points are determined. Each step is identified and the saved data stream resampled at a precise rate of approximately 100 samples per step.

It should be noted that multiple parameters regarding the user's gait can be extracted from the data produced by the sensor module depending on the type of sensors used in the sensor module. These parameters can then be used as points of comparison with the signature (or characteristic) data mentioned above. Some of these parameters may be:

Actual forces

Relative (normalized) forces.

Ratios between the peak forces in the eight sensor zones

Relative timing between forces on each sensor (strike and release sequence)

Average rate of change of force on each sensor zone

Maximum rate of change of force on each sensor zone

Frequency spectrum of the waveform from each sensor (ratio of values of harmonics derived from a Fourier transform)

Heel strike and toe lift off impact forces in the three axes.

Data waveform shape matching (waveform shape matching)

The parameters extracted from the data stream may then be compared directly or indirectly with the signature data noted above.

In one comparison scheme, the parameters extracted are used to derive a shape or loop, the characteristics of which can the compared with characteristics of a signature loop or shape. The use of a loop or shape allows for an indirect comparison between the data read by the sensor module and the signature or characteristic data. As well, it allows for more complex comparison schemes and for easier use of tolerances in the comparison.

For this comparison scheme, data from two different sensors are read by the data processing module. The two data sets (one from a first sensor and a second from a second sensor) are correlated with one another to synchronize the readings. This is done so that the data readings are synchronized in their time indices. Once synchronized, readings taken at approximately the same time index are matched with one another. Thus the result is that a data reading from sensor A taken at time t1 is mated with a data reading from sensor B taken at time t1. The mating step results in a set of pairs of data readings from two different sensors.

It should be noted that a preferable preliminary step to the correlation step is that of applying a low pass filter to both sets of data. Such a low pass filter would remove the low frequency components of the signals and would provide cleaner and easier to process signals.

As an example of the processing performed on the data streams received from the sensor modules, FIGS. 3-8 are provided to aid in the understanding of the process. Prior to any processing, data streams are first received from all of the sensors for a given fixed duration. For each sensor, the data stream for the given duration is saved by the data processing module. The resulting waveform for each sensor is then partitioned to determine discrete steps taken by the user. If the sensors are force/pressure sensors, this partitioning may be done by searching for peaks and valleys in the waveform. Each peak would denote a maximum force applied to the sensor and each valley would denote a minimum (if not absence) of force. Each step can then be seen as two valleys with a peak in between, representing the user's foot in the air, the actual step, and then user lifting his/her foot again. Alternatively, depending on how the system is configured, each step might be seen as two peaks bookending a valley.

Figure 3:
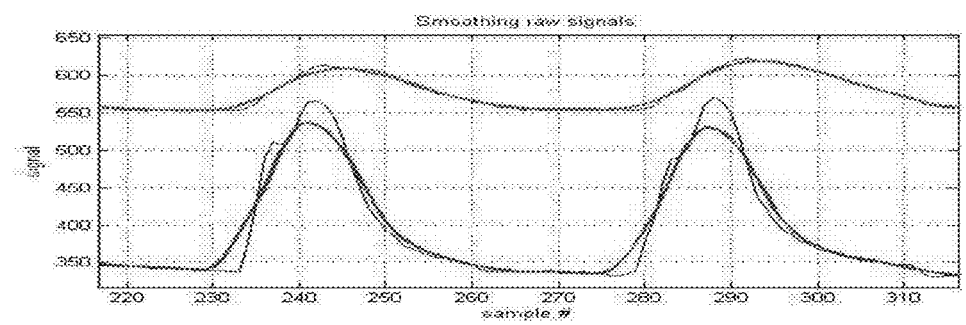
FIG. 3 illustrates raw data waveforms and data waveforms after a low pass filter has been applied.

Referring to FIG. 3, two raw data streams is shown at the bottom of the plot. After a low pass filter is applied to the signals, the smoother waveforms are shown at the top half of FIG. 3. From FIG. 3, one can see maximum force applied to the force pads for the two steps captured by the waveforms.

Once the discrete steps have been delineated in the data received from each of the sensors, each step for each sensor is then resampled to arrive at a predetermined number of data samples for each step. For the resampling, each sample is for a predetermined time frame and at a predetermined point in time in the current step. As an example, if each step lasts approximately 0.1 sec and 100 samples per step are desired, then the first sample is taken at the first one thousandths of a second in the waveform and the second sample is taken at the second one thousandths of a second and so on and so forth. This method essentially synchronizes all the samples such that it would be simple to determine all samples (from all the sensor readings) taken at the first one thousandths of a second or all samples taken at the first fiftieth one thousandths of a second as the relevant samples would all be similarly time indexed.

Once the different data waveforms from the different sensors have been synchronized, any two of the sensors and the data they produced can be selected for comparison with the signature data noted above and which may be stored in the data storage module. Depending on the configuration of the system, the signature or characteristic data stored in the data storage module may take numerous forms. In one example, multiple data sets/pairs (either filtered or as raw data) from the user may be stored so that a signature loop may be derived from the signature data whenever the characteristics of that signature loop are required. For this example, all the data pairs from all sensors would be stored so that any two sensors may be selected. Alternatively, the specific characteristics of the signature loop may be stored as the signature or characteristic data if one wanted to dispense with determining the signature loop every time a comparison needs to be made. As another alternative, only the data relating to the average signature loop derived from the user may be stored as signature data. Of course, if multiple sensors are to be used, then most possible average signature loops from the user data would be stored. In one other alternative, all the raw data (either filtered or not) from the user's steps may be stored as signature data. Such a configuration would allow for the greatest amount of flexibility as the system could randomly select any two of the sensors to be used and the signature data from the user would be available for those two sensors. As noted above, this configuration would require that the signature loop be calculated every time a comparison is required. The signature data may, if desired, be stored in encrypted format.

Once two of the sensors are selected from the sensors available in the sensor module (in this example the sensor module has 8 sensors, one for each of the eight zones illustrated in FIG. 2B), the resampled data for those two sensors are then mated with one another. This means that each time indexed sampling will have two points of data, one for the first sensor and another for the other sensor. These pairs of sensor readings can thus be used to create a characteristic loop. As an example, if sensors A and B are used and n denotes an index, then A[n] denotes the nth sampled reading from the waveform received from sensor A for a specific step. Similarly, B[n] is the nth sampled reading from the waveform received from sensor B for the same specific step. {A[n], B[n]} thus constitutes a data pair for the nth reading for that particular step. Plotting all the data pairs for a particular step, with readings from one sensor being on one axis and readings from the other sensor on the axis, results in an angled loop-like plot (see FIGS. 4-8 as examples). For pressure/force readings, this is not surprising as the force exerted by the foot in a particular step increases to a maximum and then decreases to as minimum as the person increases the weight the place on the foot and then removes that weight as the step progresses.

Figure 4:
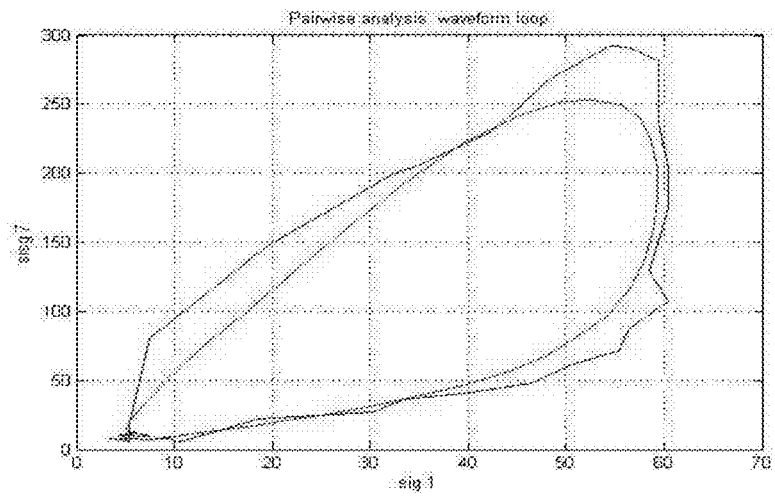
FIG. 4 illustrates loops plotted using raw data and filtered data.

Once the data pairs have been created, a plot of the resulting loop can be made. As noted above, FIG. 3 shows the waveforms for two signals—the lower waveform being the raw data stream waveforms for 2 signals and the upper waveforms for the same 2 signals after a low pass filter has been applied. FIG. 4 shows a plot of the two sets of waveforms in FIG. 3. One loop in FIG. 4 is derived from the raw signal waveforms in FIG. 3 while the other loop is derived from the low pass filtered waveform in FIG. 3. As can be seen in FIG. 4, a smoother loop is produced by the low-pass filtered signals. It should be noted that the x-axis in FIG. 4 contains the values gathered from the first sensor selected while the y-axis contains the values gathered from the second selected sensor. It should be noted that while the embodiment discussed uses only a pair of sensors, the concept is applicable for 3, 4, or any number of sensors. If data from 3 sensors were used, then, instead of a 2D loop, a 3D loop may be created as a characteristic loop.

Figure 5:
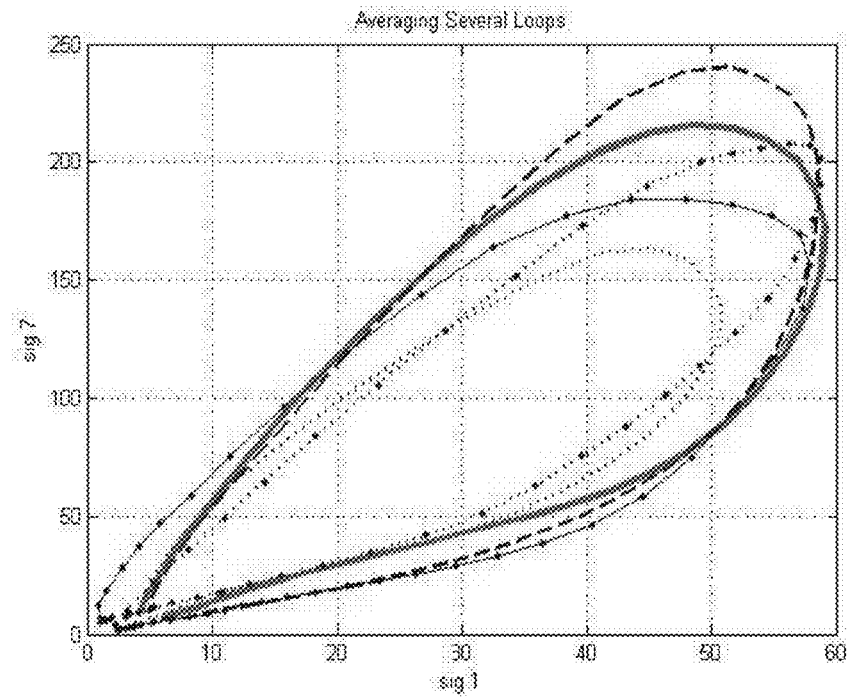
FIG. 5 illustrates a number of characteristic for different sets of data from the same user as well as an average characteristic loop derived from the other loops.

It should be noted that a loop can be formed for each one of the steps captured by the sensors. An averaged loop can be derived from the various loops formed from all the steps captured by the sensors. Referring to FIG. 5, the various loops from the various steps can be seen on the plot. An average loop (see darker loop in FIG. 5) is derived from all the loops captured using the low pass filtered waveforms. Multiple methods may be used to determine the average loop. However, in one embodiment, the points for the average loop are derived by averaging the various readings for each particular time index. As such, if the data pairs are as (An[i],Bn[i]) with An[i] denoting the nth reading for sensor A at time index i and Bn[i] denoting the nth reading for sensor B at time index i, then to derive the data reading for sensor A for the average loop for time index i, one merely averages all the An[i] where n=1, 2, 3, etc., etc. Similarly, for data reading for sensor B for the average loop for time index i, one merely averages all the Bn[i] where n=1, 2, 3, etc., etc. By doing this for all the multiple time indices, an average loop is derived from all the characteristic loops.

Figure 6:
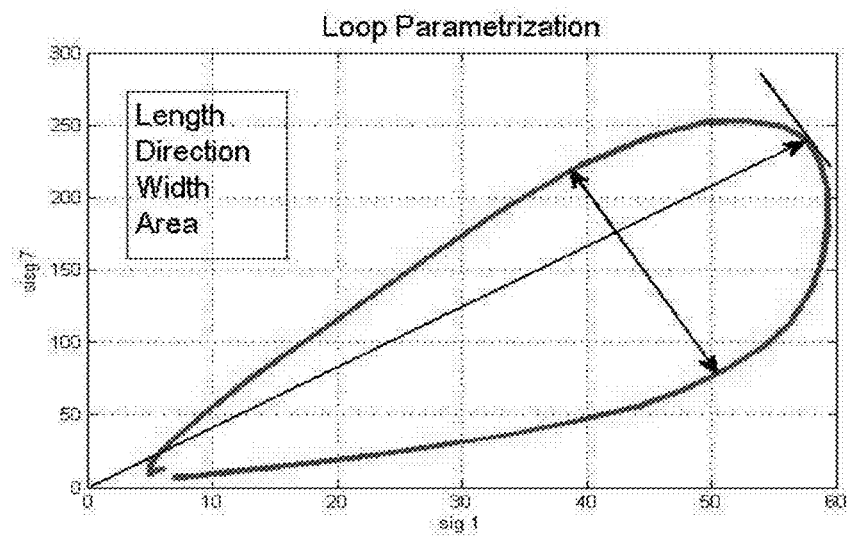
FIG. 6 illustrates the different characteristics which may be derived from the characteristic loops.

Once the average loop has been derived, the characteristics of that average loop can be determined. Referring to FIG. 6, some of the characteristics of the average loop can be seen. The length of the loop (measured from the origin), the width of the widest part of the loop, and the area occupied by the loop are just some of the characteristics which may be determined from the loop. As well, the direction of the loop (whether it develops in a clockwise or anti-clockwise manner) may also be seen as a characteristic of the loop. Another possible characteristic of the loop may be the angle between a ray from the origin to the farthest point of the loop and one of the axes of the plot. Additional characteristics of these loops may, of course, be used depending on the configuration of the system.

Figure 7:
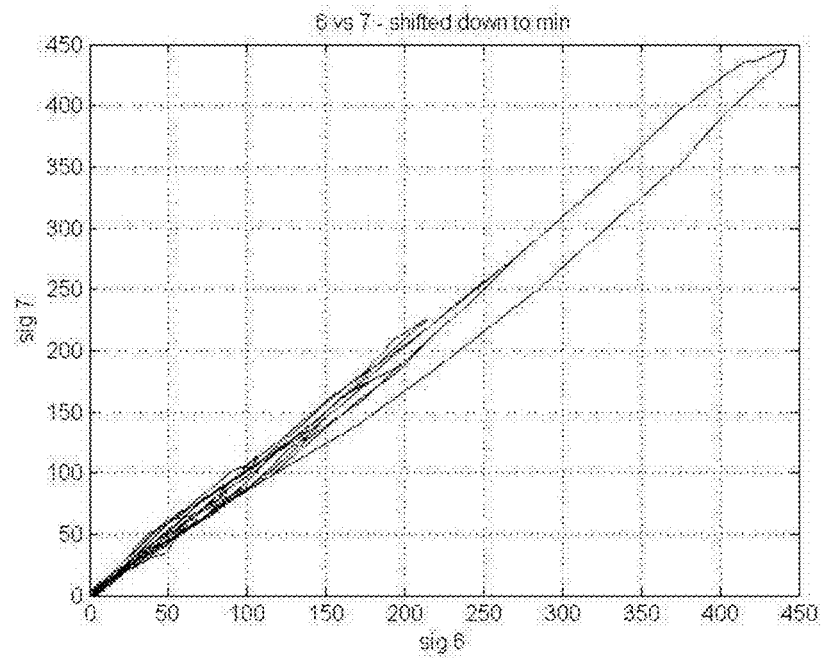
FIG. 7 illustrates characteristic loops using highly correlated data.

As another example of possible loops, FIG. 7 shows loops resulting from highly correlated data from the sensors. Such highly correlated data may produce loops that, at first glance, may not be overly useful. However, even such lopsided loops may yield useful characteristics. As an example, the amplitude from the furthest point may be used for an initial assessment of static of dynamic weight distribution.

Once the average loop for the steps captured by the sensors is determined, the characteristics for this average loop can be derived. Once derived, the same process is applied to the signature data stored in the storage module. The characteristics for the resulting signature loop (from the signature data) are then compared to the characteristics of the average loop from the data acquired from the sensors.

Figure 8:
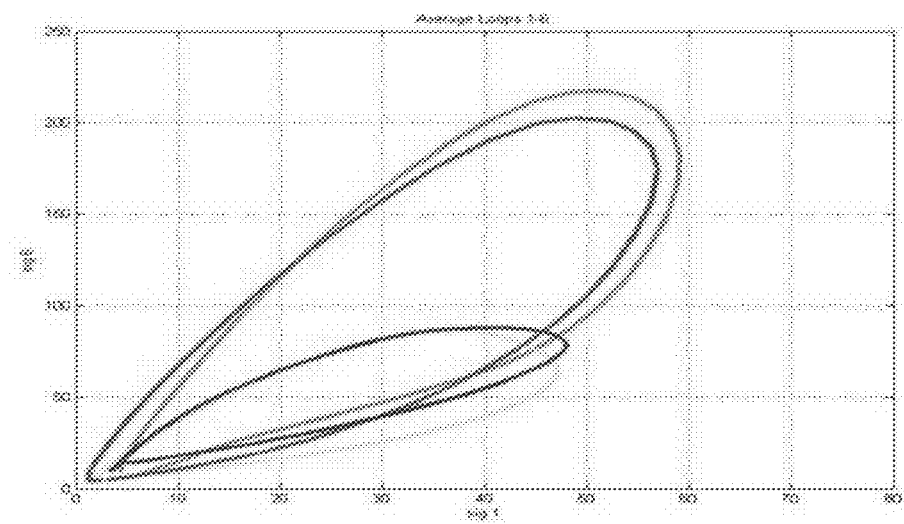
FIG. 8 shows average characteristic loops for different users.

Referring to FIG. 8, a comparison of two average loops from the gait of two individuals is illustrated. As can be seen, the characteristics of the two loops are quite different. One loop is clearly larger (more area), longer (length of loop), and wider (width at widest of the loops) than the other loop. It should be noted that custom tolerances can be applied to the comparison. Depending on the tolerance applied, the comparison can be successful (the characteristics match within the tolerances) or unsuccessful (even within the tolerances, there is no match). It should be noted that, as noted above, comparisons can be made for loops from a single user with data taken at different times. As an example, a user may have gait data taken at a first visit to a physician. Later gait data sets can then be taken for the same user at subsequent visits to the physician. The loops derived from the initial gait data set and the subsequent gait data sets can then be compared to determine how a particular treatment regimen has affected that user's gait over time.

Regarding tolerances, these can be preprogrammed into the system and can be determined when the signature data is gathered. As an example, a tolerance of 15% may be acceptable for some users while a tolerance of only 5% may be acceptable. This means that if the calculated characteristic of the average loop is within 15% of the calculated characteristic of the signature loop, then a match is declared. A match would indicate that there is no relevant difference between the loops being compared. Similarly, if a tolerance of only 5% is used, then if the calculated characteristic of the average loop is within 5% of the calculated characteristic of the signature loop, then a match is declared. Of course, if the calculated characteristic of the average loop is not within the preprogrammed tolerance of the calculated characteristic of the signature loop, then a non-match is declared. A non-match would indicate that there is a relevant difference between the loops being compared. A match may indicate that, for example, a treatment regimen has affected a user's gait between the time the first set of gait data was gathered to the time the second set of gait data was gathered. A non-match may, of course, indicate that the treatment regimen has not affected the user's gait.

It should also be noted that, in addition to the tolerances noted above, the system may use a graduated system of matches or matching. This would mean that a level of confidence may be assigned to each match, a high level of confidence being an indication that there is a higher likelihood that there is a match between the two sets of data derived from the average loop and the signature loop. A match can then be declared once the level of confidence assigned is higher than a predetermined level. A non-match can similarly be declared once the level of confidence is lower than a predetermined level. A level of indecision can be declared when the level of confidence is between the two preset levels for match and non-match. If a set of data falls within the gray area or an area of indecision between the two preset levels, then more data can be retrieved from the sensors and this data can be processed as above to arrive at a determination of a match or a non-match.

It should further be noted that, as an alternative, instead of matching or not matching two loops derived from a user's gait data, the amount of difference between the two loops can be determined. A significant difference between the characteristics of the two loops, preferably derived from data gathered from the same user using the same sensors in the sensor module at different times, would indicate a change of some sort. A significant difference between such two loops would indicate a significant change from the time the first data set was gathered to the time the second data set was gathered. As noted above, this could indicate that a treatment regimen was having an effect on the user's gait. It may also indicate that a user's condition is either progressing or regressing. The characteristics for which a difference may be found may, as noted above, include the size of the loops, the angle of the loops to one of the axes of the plot, the perimeter of the loops, the area covered by the loops, as well as other characteristics. A tolerance may, of course, be built into the comparison subroutine. As an example, if the tolerance is set at 2%, if a characteristic of two loops are within 1% (i.e. less than 2%) of each other (e.g. the sizes of the two loops) then no difference is concluded.

For greater clarity, the difference between two loops may be quantified and, depending on how great the differences are, alarms or other steps may be taken. As an example, if the area of a loop derived from a user's initial data set is compared with the area of a loop derived from a data set gathered a few months later, the differences may be significant. If there is no appreciable difference, then one can conclude that no change has occurred in the user's condition. If, on the other hand, the second data set has a much larger area (e.g. 25% greater area than the area covered by the loop from the first data set), this may indicate that the user is walking slower or that the user is placing more pressure on his feet with each step. Depending on the user's medical condition, this may indicate a progression (getting worse) or a regression (getting better) of that condition. It may also indicate that a treatment regimen being used may not be effective. A threshold may thus be programmed so that if the difference in value of a characteristic being compared between two loops exceeds a specific amount or percentage, an alarm may be activated.

Regarding the programming or storage of the signature or characteristic data into the system, this is preferably done when the user who is to be diagnosed is first encountered. This first data set can provide a baseline set of data to be used in comparison with subsequent data sets. This is done by having the user use the insole/sensor module by taking a specific number of normal steps. These steps are then captured in the system and are stored as signature/characteristic or baseline data. Once stored, the signature data can be retrieved and various characteristics of the signature data (by way of the signature loop) can be determined as described above. As described above, the signature data stored may take any number of forms. The signature data may be the raw data gathered from the user when s/he took the specific number of normal steps. Alternatively, the signature data may be the filtered version of the raw data or it may be the various characteristics of the various possible signature loops. Also, instead of the raw data which forms the waveforms, the waveforms themselves may be stored as signature data. The signature data may take any form as long as the characteristics of the signature loops may be derived from or be extracted from the signature/characteristic/baseline data.

Figure 9:
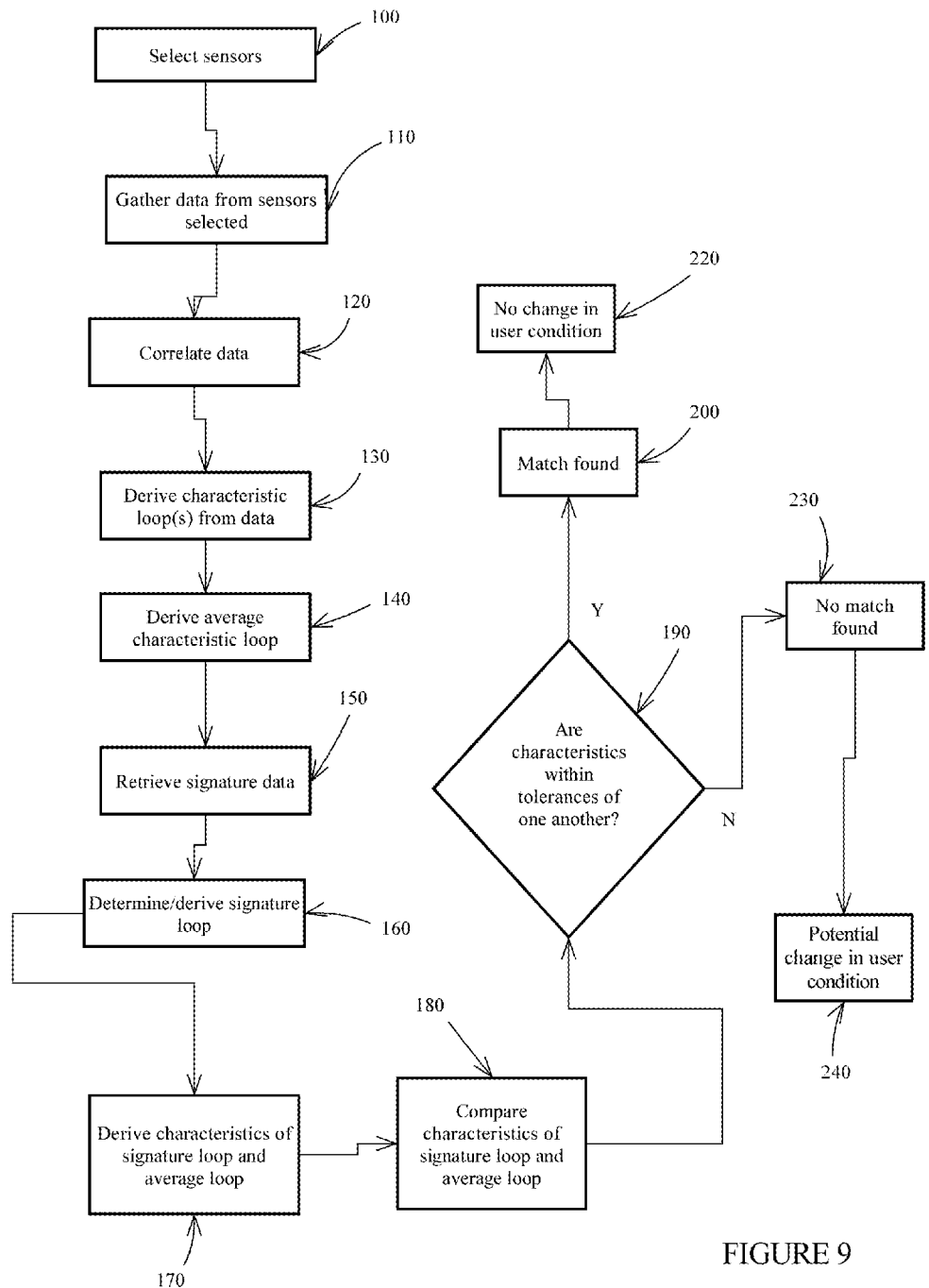
FIG. 9 is a flowchart illustrating the steps in a method according to another aspect of the invention.

Referring to FIG. 9, a flowchart of the process described above is illustrated. To store the signature data into the system, the initial step 100 in the process is that of selecting two of the sensors to be used in the comparison process. As noted above, the sensors are, in one embodiment, inserted or installed in a user's show. Once the sensors have been selected, data is gathered from these sensors as the user walks normally (step 110). Once gathered from the sensors, the data is then correlated with one another to form the data pairs noted above (step 120). This means that data points from one sensor is mated with data points from another sensor. With the data pairs in hand, at least one characteristic loop can then be created/derived from the data pairs (step 130). Depending on the configuration, discrete steps may be separated from one another so that each step may have its own characteristic loop. Alternatively, an average characteristic loop may be derived from the data values from the sensors. Once the average characteristic loop has been found (step 140), the signature data can be retrieved (step 150). The signature data, depending on configuration can then be used to determine the signature loop (step 160). The characteristics of both the average characteristic loop and the signature loop can then be calculated or derived from the two sets of data (step 170). The characteristics are then compared (step 180), taking into consideration the preprogrammed tolerances. If the characteristics from the two sets of data are the same (step 190) (within the preprogrammed tolerances) then a match is found (step 200) indicating no change in the user's condition (step 210). If they are not within the preprogrammed tolerances, then no match is found (step 220) and a potential change in the user's condition is indicated (step 230).

The process may also be seen as eight specific steps.

The first processing step after retrieving the data is one where the pair sensor signals are filtered applying DFT (Discrete Fourier Transform) based low-pass filter. The cut-off frequency of the filter is defined taking into account a Nyquist frequency (related to the sampling rate) on the high end, and a main signal frequency (related to the walking speed of the individual) on the low end. Walking frequency estimation is also a part of the described processing step.

Using an FFT (Fast Fourier Transform) implementation technique and sync-filter as a benchmark, a low pass filter with flat pass-band (low ripple) high stop band attenuation may be used. Additional advantage is taken from the use of non-causal filters since the hard-real-time processing is not required (signals are registered first and then filters are applied).

The second processing step is a construction of the characteristic loop for the chosen pair of signals. The characteristic loop is an ordered set of points with coordinates (X(i),Y(i)) where X(i) is a first chosen signal and Y(i) is a second chosen signal, i is an index corresponding to the sample number.

An autonomous loop is constructed for the time period (subset of all samples) corresponding to the evolution of both signals from low level to maturity level and back to low level. Such a construction is possible since the low level of all signals have a non-empty intersection corresponding to the foot not contacting the ground.

Due to quasi-periodicity of all signals resulting from the nature of human walking, characteristic loops can be constructed autonomously for several periods in time. Although initially defined for raw signals, autonomous loops can then be constructed for smoothed signals (obtained after the first step processing described above).

The third processing step is that of averaging the loops. Several loops are constructed according to the recording of several steps while the person is walking. Those steps and respectively those loops are subject to significant variations. It has been found that only the average loop provides a stable and robust characteristic of human walking.

Averaging of the loops is done by artificially synchronizing several loops (as corresponding to several steps) followed by weighted averaging of the synchronized loops. Weight factors are computed according to the phase shifts from an estimated reference signal (main walking frequency—as per first processing step).

The fourth processing step consists of extracting initial geometrical parameters from the average loop such as loop length, loop width, direction of longitudinal axes, loop directionality (clockwise or counter-clockwise) and the area inside the loop. Other characteristics/parameters which can be used are the variance of each parameter listed above as computed for individual walking steps and as compared to the average value (computed from average loop).

Other parameters which can be extracted may use:
  Geometrical method—identify a point on the loop farthest from the origin (let us call it M) this point is further used to find the length (|OM|) and direction of the longitudinal axis (OM), the width is defined as maximal projection onto the line perpendicular to OM Statistical approach—considering the loop as the cloud of points, the elliptical fit (correlation analysis) can be applied followed by extraction of the parameters of the fitted ellipse (major and minor axis length and orientation).

Regarding loop directionality, the directionality of the loop is related to the phase shift between signal Y and signal X. Namely, the loop is clockwise if Y signal grows from low level to maturity first, followed by the growth of X signal.

The fifth processing step consists of analysing special cases. It is worth noticing that in some cases, for some pairs of signals, the construction of the loop as described above might yield less than perfect results. This may result in a "degenerated loop" due to a high correlation between signals. The "loop" in such case is located very close to the diagonal. For this case only the point farthest from the origin is actually computed (corresponding to maximal amplitude of both signals).

The sixth processing step consists of comparing the loops computed from 2 separately recorded data. It has been found that the high discrimination efficiency of the proposed parametric representation of the pair-wise average loops (see FIG. 8 as an example). Namely, for several pairs of signals/sensors extracted from the set of 8 signals/sensors, the average loops constructed from the smoothed signals stably demonstrate significant similarities when constructed from the data corresponding to the same individual as well as significant differences from average loops constructed for different individuals.

The seventh processing step consists of combining the results of the comparison of several (up to all 56 possible pairs from 8 different sensors/signals) pairs in order to produce a highly efficient discriminate function. Results from various pairs are first weighted according to the number of parameters that can be robustly estimated to support the comparison of the loops. Finally, the results from various pairs can be fused using Dempster-Shaefer framework for an estimation of the likelihood that 2 individuals who used the system are identical or not.

The system described above may be used in any number of ways. The system can be used to determine a user's medical condition as well as whether a treatment regimen is effective or not. As is well known, for some medical conditions, the progression of the condition affects a person's gait. Similarly, the regression of the condition also affects the person's gait. As such, by comparing a user's baseline gait data with subsequently gathered gait data, the user's condition can be monitored. If no change in the user's gait is detected, then the medical condition has neither progressed nor regressed. If there is a noticeable change in the user's gait (as evidenced by differences in the loops derived from the baseline gait data and the subsequent gait data) this may indicate progression, regression, efficacy of a treatment regimen, or any number of health changes in the user. Of course, the determination as to which change has occurred needs to be determined by experimentation and clinical tests so as to determine correlation between the loop differences, the types of differences, the amount of the difference, and the different conditions and changes in the condition.

In another embodiment, all of the data processed by the data processing module may be internally encrypted so that external systems would not be privy to the raw data transferred between the sensor module and the data processing module. Prior to transmitting the raw data from the sensor module to the data processing module, the data may be automatically encrypted. As can be understood, the data processing module may be physically remote from the sensor module and, as such, the data transmissions between these modules may be vulnerable to the outside. In another embodiment, the data processing module is contained within the insole to ensure that any data transfers between the modules are slightly more secure.

In another embodiment, any data transfers or communications between the system and any outside diagnostic systems are encrypted, preferably with one time encryption schemes, to ensure that outsiders are not able to intercept any usable data. Such precautions would preserve the system user's privacy.

The system of the invention may be used to periodically determine if a user's medical condition is progressing or regressing. As well, it may be used to determine if any treatment regimen to which the user is being subjected to has had an effect on the user or on the user's gait. The user's baseline gait data may be gathered when the user first visits a facility properly equipped with the system of the invention. Subsequent visits by the user would entail gathering subsequent gait data sets. The loops derived from the baseline gait data set and the subsequent gait data sets can be compared with one another to view any variances between the user's gait data. The amount of change in the loop characteristics from the different data sets can provide an indication as to the degree of change in the user's condition. Large changes in the loop characteristics may indicate an acceleration in the user's condition and may also indicate whether the user's treatment regimen (which may include pharmacological treatments) is effective or not.

It should be noted that any useful data processing means may be used with the invention. As such, ASICs, FPGAs, general purpose CPUs, and other data processing devices may be used, either as dedicated processors for the calculations or as general purpose processors for a device incorporating the invention.

The method steps of the invention may be embodied in sets of executable machine code stored in a variety of formats such as object code or source code. Such code is described generically herein as programming code, or a computer program for simplification. Clearly, the executable machine code may be integrated with the code of other programs, implemented as subroutines, by external program calls or by other techniques as known in the art.

The embodiments of the invention may be executed by a computer processor or similar device programmed in the manner of method steps, or may be executed by an electronic system which is provided with means for executing these steps. Similarly, an electronic memory means such computer diskettes, CD-Roms, Random Access Memory (RAM), Read Only Memory (ROM) or similar computer software storage media known in the art, may be programmed to execute such method steps. As well, electronic signals representing these method steps may also be transmitted via a communication network.

Embodiments of the invention may be implemented in any conventional computer programming language For example, preferred embodiments may be implemented in a procedural programming language (e.g."C") or an object oriented language (e.g."C++"). Alternative embodiments of the invention may be implemented as pre-programmed hardware elements, other related components, or as a combination of hardware and software components.

Embodiments can be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or electrical communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server over the network (e.g., the Internet or World Wide Web). Of course, some embodiments of the invention may be implemented as a combination of both software (e.g., a computer program product) and hardware. Still other embodiments of the invention may be implemented as entirely hardware, or entirely software (e.g., a computer program product).

A person understanding this invention may now conceive of alternative structures and embodiments or variations of the above all of which are intended to fall within the scope of the invention as defined in the claims that follow.

We claim:

1. A method for determining changes in a user's medical condition using a foot-based gait device, said device having a plurality of sensors for gathering gait-based data, the method comprising:
   a) selecting two of said plurality of sensors, said plurality of sensors being in said device;
   b) gathering data from each sensor selected in step a);
   c) correlating data gathered from said two sensors such that data points gathered at similar instances are matched with one another to result in data pairs;
   d) determining at least one characteristic loop from said data pairs, each characteristic loop being a loop formed when said data point pairs are plotted;
   e) retrieving signature characteristic data, said signature characteristic data being derived from data resulting from biometric data previously gathered from said user, said signature characteristic data serving as a baseline set of data to be compared against data gathered from said sensors;
   f) determining a signature characteristic loop from said signature characteristic data;
   g) comparing characteristics of said at least one characteristic loop determined in step d) with characteristics of said signature characteristic loop determined in step f) to determine differences data between said characteristics of said at least one characteristic loop from step d) and characteristics of said signature characteristic loop from step f), said differences data including at least one of: loop differences, types of differences between said loops, and an amount of said differences;
   h) if a comparison of said characteristics compared in step g) produces results not within predetermined limits, determining that a change has occurred in said user's medical condition;
   i) if a comparison of said characteristics compared in step g) produces results within predetermined limits, determining that a change has not occurred in said user's medical condition.

2. The method according to claim 1 wherein said device is an insole for gathering data regarding an individual's gait.

3. The method according to claim 1 wherein step d) comprises determining multiple characteristic loops using multiple sets of data gathered from sensors selected in step a) and averaging said multiple characteristic loops to result in an average loop.

4. The method according to claim 3 wherein said average loop is compared to said signature characteristic loop in step f).

5. The method according to claim 1 further including the step of applying a filter to data gathered from said sensors prior to producing said data point pairs.

6. The method according to claim 1 wherein said characteristic compared in step f) includes at least one of:
   a length of said loops
   a width of said loops
   an angle of said loops with a given axis
   a direction of propagation of said loops
   an area of said loops.

7. The method according to claim 2 wherein said insole is removable from a shoe worn by a user.

8. A system for diagnosing a change in a user's condition, the system comprising:
   a sensor module comprising at least one sensor for gathering gait-based biometric data from said user, said sensor module being in a single device having at least two sensors;
   a data storage module for storing data relating to a signature loop, said signature loop being a loop resulting from a plot of data pairs derived from data gathered from said sensor module when said user uses said system, said signature loop being a baseline against which subsequent characteristic loops are compared;
   a data processing module for receiving data from said sensor module, said data processing module being for determining characteristic loops from said data received from said sensor module and for comparing characteristics of said characteristic loops with characteristics of said signature loop, said characteristics of said characteristic loops being compared with characteristics of said signature loop to to determine differences data between said characteristic loops and said signature loop, said differences data including at least one of: loop differences, types of differences between said loops, and an amount of said differences;
   wherein
   a change in said user's medical condition is indicated when said characteristics of said characteristic loops are not within predetermined limits of said characteristics of said signature loops;
   an indication that said user's medical condition is unchanged when said characteristics of said characteristic loops are within said predetermined limits.

9. The system according to claim 8 wherein said sensor module comprises an insole for use with said user's shoe.

10. The system according to claim 9 wherein said at least one sensor detects and measures a force applied to said sensor module by a foot of a user as said user is walking.

11. The system according to claim 8 wherein said at least one sensor detects and measures pressure applied by a user's foot to said sensor as said user is walking.

12. The system according to claim 9 wherein said at least one sensor detects a force applied to different areas of said sensor module by said user's foot as said user is walking.

13. The system according to claim 9 wherein said at least one sensor comprises a plurality of sensors, each sensor being for detecting and measuring an amount of force applied to different areas of said sensor module by said user's foot.

14. The system according to claim 9 wherein said at least one sensor comprises a strain gauge configured and adapted to measure forces applied to different areas of said insole by said user's foot.

15. The system according to claim 9 wherein said insole is removable from a user's shoe.

\* \* \* \* \*